(12) United States Patent
Stein et al.

(10) Patent No.: US 6,258,526 B1
(45) Date of Patent: Jul. 10, 2001

(54) EX-VIVO TEST KIT FOR TESTING THE EFFECTIVENESS OF REVERSERS OF MULTIDRUG RESISTANCE

(75) Inventors: Wilfred Donald Stein; Miriam Viviana Kott, both of Jerusalem (IL)

(73) Assignee: M.D.R. Test LTD (IL)

( * ) Notice: Subject to any disclaimer, the term of this patent is extended or adjusted under 35 U.S.C. 154(b) by 0 days.

(21) Appl. No.: 09/487,429

(22) Filed: Jan. 19, 2000

(51) Int. Cl.⁷ .............................. C12Q 1/00; C12Q 1/70; G01N 33/53; C12N 11/00; C12M 1/34
(52) U.S. Cl. ................ 435/4; 435/5; 435/6; 435/7.1; 435/7.9; 435/174; 435/177; 435/287.1; 436/809
(58) Field of Search ................ 435/4, 174, 177, 435/5, 6, 7.9, 7.1, 287.1; 436/809

(56) References Cited

U.S. PATENT DOCUMENTS

| | | | |
|---|---|---|---|
| 5,403,574 | * 4/1995 | Piwnica-Worms | 424/1.65 |
| 5,543,423 | * 8/1996 | Zelle et al. | 514/332 |
| 5,670,507 | * 9/1997 | Rice et al. | 514/263 |
| 5,686,578 | * 11/1997 | Goldenberg | 530/387.3 |
| 5,723,459 | * 3/1998 | Armistead et al. | 514/237.8 |
| 5,851,789 | * 12/1998 | Simon et al. | 435/32 |

OTHER PUBLICATIONS

Hollo et al. Transport properties of the multidrug resistance–associated protein (MRP) in human tumour cells. FEBS Letters. vol. 383, No. 1–2 (1996) pp. 99–104.*

Ghetie et al. Anti–CD19 antibodies inhibit the function of the P–gp pump in multidrug–resistant B lymphoma cells. Clinical Cancer Research. vol. 5, No. 12 (1999) pp. 3920–3927.*

Broxterman et al. Multidrug resistance proteins and other drug transport–related resistance to natural product agents. Current Opinion in Oncology. vol. 7, No. 6 (1995) pp. 532–540.*

Shapiro et al. P–glycoprotein–mediated Hoechst 33342 transport out of the lipid bilayer. European Journal of Biochemistry. vol. 250, No. 1 (1997) pp. 115–121.*

* cited by examiner

*Primary Examiner*—Long V. Le
*Assistant Examiner*—Kartic Padmanabhan
(74) *Attorney, Agent, or Firm*—Ladas & Parry

(57) ABSTRACT

The invention provides an ex-vivo test kit for testing the effectiveness of reversers of multidrug resistance in the blood, serum or plasma of a patient containing the reversers, the kit comprising, a plurality of cell membranes from highly drug-resistant cells, the cell membranes containing proteins which pump drugs and the membranes being respectively attached to a plurality of support surfaces, and a dye which provides a light signal, which dye is pumped by the proteins contained in the membranes.

19 Claims, No Drawings

EX-VIVO TEST KIT FOR TESTING THE EFFECTIVENESS OF REVERSERS OF MULTIDRUG RESISTANCE

BACKGROUND OF THE INVENTION

The present invention relates to an ex-vivo test kit for testing the effectiveness of reversers of multidrug resistance, to methods for the use thereof and to methods for the preparation of the components thereof. More particularly, the present invention relates to an ex-vivo test kit for testing the effectiveness of reversers of multidrug resistance in the blood, serum or plasma of a patient containing said reversers.

DESCRIPTION OF THE RELATED ART

Most people who die as a result of having cancer do so because their tumors have either developed resistance to chemotherapy or were resistant to begin with. Therefore, the development of drug resistance in a patient is still a major barrier to the effectiveness of chemotherapy treatment of cancer. Until ways to entirely prevent cancer are found, overcoming drug resistance will remain the main avenue for saving millions of lives. Great efforts have been invested in the development of accessory drugs which can block multidrug resistance and hence restore effectiveness to the chemotherapeutic regime.

A certain cell membrane protein, P-glycoprotein, is an important contributor to multidrug resistance in a substantial number of tumors. There are other ways by which cancers develop resistance to chemotherapeutic drugs, e.g., the presence in their cell membranes of the Multidrug Resistance-associated Protein, the Mitoxantrone Resistance protein and Lung Resistance Protein systems, as well as other, non-membrane systems. All these membrane proteins have a similar action, i.e. they are able to pump out anti-cancer drugs and many other drugs from the cells in which they are found. In this way, a low concentration of such anti-cancer drugs are retained in the cancer cell, thus defeating the aim of the clinician which is to keep the anti-cancer drug in as high a concentration as possible within the cancer cell. It has been postulated and it is believed that these pump proteins appear in the membranes of the cancer cells as a typical response of an aggressive cancer cell which tries all ways to survive against the efforts of the clinician. In this case, the cancer cell evolves the ability to express the pump proteins in its membrane. Great efforts by major pharmaceutical are being made in order to find clinically-useful reversers of multidrug resistance, i.e. agents that can block its action, allowing formerly resistant cells to renew the accumulation of drugs. Many reversers have been identified and a few are now in clinical trial which are used in combination with an appropriate anti-cancer drug.

It has been found that many of the reversers that have been used in clinical trials have not been effective simply because they are bound in the patient's plasma and are not able to enter the membrane of the cancer cells and therefore are not in a position to counteract the pump that is pumping out the anti-cancer drug.

The present inventor has previously reported the development of an assay, using living P-glycoprotein-containing cells grown outside the body in cell culture (Ayesh, S. E. Lyubimov, N. Algour, and W. D. Stein. 1996.) Reversal of P-glycoprotein is greatly reduced by the presence of plasma but can be monitored by an ex vivo clinical assay. (Anti-Canc. Drugs 7:678686), which enabled the immediate measurement in a sample of the plasma taken from a patient of the effectiveness of any reverser of the membrane pumps. This assay, while reliable and useful proved to be cumbersome, and required that there be available at all times a supply of these cultured cells. Hence it is not suitable as a routine clinical assay for the hospital laboratory.

BRIEF SUMMARY OF THE INVENTION

With this state of the art in mind, there have now been developed according to the present invention, an ex vivo test, in kit form, which can be used to test the effectiveness of reversers, directly in the plasma of patients that are receiving the combined therapy. With the presently proposed kit, which is designed as an ex vivo assay to be readily usable in standard clinical laboratories, clinicians will be able to treat patients with reversers of multidrug resistance and, simultaneously, assay in plasma, serum or blood samples from such patients the effectiveness of the reversers in the plasma, serum or blood of the patient. The clinician will be able to try different reversers and test the effectiveness of each of these, and choose the most effective, before the patient even receives the chemotherapy. In addition, the pharmokinetics of the drug can be readily and safely studied in the patient so as to ascertain the time/dose requirements for the reverser in question. Before the patient receives chemotherapy, he/she will be treated with the reverser, over a twenty-four hour period, and blood samples will be taken for measuring how much of the reverser is available, free to block the patient's multidrug resistance pump. In this way, the doctor looking after the patient will be able to know in one day whether his/her patient has received an effective dose of the blocker rather than waiting months until it can be determined whether or not the tumor has been destroyed. If, by the present test, the doctor can show that the dose of reverser received was not effective, a higher dose or another reverser can be immediately substituted and the effectiveness of this second treatment again checked by the serum assay. All this will be able to be ascertained before the patient is treated with the chemotherapeutic agent, with all of its attendant dangers and discomforts. Use of the presently proposed assay should therefore greatly increase the success of cancer treatments, increasing the health and well-being of many cancer sufferers all over the world.

In addition, the assay of the present invention can be used by the pharmacological companies in testing and developing new blockers for other multidrug resistance systems and can be used in high-throughput searches for such blockers.

Furthermore, the present kit enables the effectiveness of P-glycoprotein reversers to be tested against both of the two sites for substrate or reverser binding that Shapiro and Ling have identified as being involved in drug pumping by P-glycoprotein (Shapiro, A. B. and V. Ling. 1995. Reconstitution of drug transport by purified P-glycoprotein. J. Biol. Chem. 270:16167–16165). These two sites have different affinities for the various ligands of P-glycoprotein and the kit of the present invention can enable the effectiveness of any reversers to be ascertained in serum against each of these two sites.

DETAILED DESCRIPTION OF THE INVENTION

Thus, according to the present invention there is now provided an ex-vivo test kit for testing the effectiveness of reversers of multidrug resistance in the blood, serum or plasma of a patient containing said reversers, said kit comprising, a plurality of cell membranes from highly drug-resistant cells, said cell membranes containing proteins which pump drugs and said membranes being respectively attached to a plurality of support surfaces, and a dye which provides a light signal, which dye is pumped by said proteins contained in said membranes.

In preferred embodiments of the present invention said dye is a fluorescent dye which provides a fluorecence signal.

The assay of the present invention uses preparations of cell membranes from highly drug-resistant cells, grown in cell culture and is designed to allow the measurement of the clearance, or the absorption, of fluorescent dyes from such membranes. The membranes are affixed to paper discs or to the sides and bottoms of, the wells of 96-well or 384-well plastic cell culture dishes.

Thus, in a first preferred embodiment of the present invention said surfaces are the surfaces of a plurality of wells.

In a second preferred embodiment of the present invention said surfaces are a plurality of plastic, comb-like teeth.

In a third preferred embodiment of the present invention said support surfaces are a plurality of filter paper elements and preferably said filter paper elements are sized to be individually inserted in the wells of a multi-well plate.

In a further aspect of the present invention, there is provided a method for testing the effectiveness of reversers of multidrug resistance in the blood, serum or plasma of a patient containing said reversers, said method comprising providing a plurality of cell membranes from highly drug-resistant cells, said cell membranes containing proteins which pump drugs and said membranes being attached to a plurality of support surfaces and a fluorescent dye which provides a fluorescence signal, which dye is pumped by said proteins contained in said membranes, and bringing said membrane-containing support surfaces into contact with the blood, serum or plasma of a patient containing said reversers, adding reagents for activating said pump and noting the results thereof.

As stated, the assay of the present invention uses membranes, prepared from cells grown in cell culture, that have been chosen so as to contain high amounts of the proteins that convey multidrug resistance. These membranes are prepared by breaking open the cells and then separating the membranes by differential centrifugation, using standard procedures. They are then affixed (a) to plastic cell culture dishes (ELISA plates) which optionally have been previously coated with polylysine at concentrations that have shown to be optimal for each cell type; or (b) to plastic strips ("combs") which have been coated with polylsine in the same way, or (c) to nitrocellulose paper discs. For (a) and (b) the cell membranes, in suspension in a standard saline-containing medium, are held in contact with the polylysine coated plates or strips for one hour at 37° C. Some 5 to 10% of the membrane material becomes fixed to the plate. The membrane-containing excess medium is removed and transferred to a second plastic support surface. This process is repeated until most of the membrane material has been adsorbed onto the polylysine-coated plates or strips. For (c), discs of nitrocellulose paper are dipped into suspensions of the cell membranes when most of the membrane material becomes adsorbed to the paper.

Tests carried out according to the present invention show that the membranes, in all these situations, are largely in the form of closed structures which has the ability to assay multidrug resistance blockers in two ways:

1) One assay depends on the fact, reported first by (Shapiro et al. ibid.) and then developed by the present inventors in great detail, that a certain fluorescent dye (Hoechst 33342) gives a large fluorescence signal when dissolved in cell membranes, but can be pumped out of these membranes, with an easily-measured reduction in the signal, when the P-glycoprotein pump is activated by the addition of the energy-providing substrate, ATP. One gets a large signal when the pump is blocked and the dye remains in the membranes that have been added to the serum. Because the dye behaves in the same way in the assay of the present invention as do the anti-cancer drugs in the patient, whether the signal is low or high in the assay will give an indication of whether the blocker is, or is not, blocking the pump, respectively, in the patient. The present invention shows that the dye Hoechst 33258 gives a far stronger signal and this dye is used routinely in the present invention.

2) The second assay depends on the fact that it has been found that the fluorescent molecule rhodamine, is well known as a substrate of P-glycoprotein (Lee, J. S., k. Paull, M. Alvarez, C. Hose, A. Monks, M. Grever, A. T. Fojo, and S. E.Bates. Rhodamine efflux patterns predict P-glycoprotein substrates in the National Cancer Institute drug screen. *Molecular. Pharmaco.* 46: 627–638, 1994).

According to the present invention it has been discovered that rhodamine can be pumped into the membrane sacs that are attached to the walls of the wells or to the strips, and can be held there when the plates or strips are washed. Its fluorescence can be measured and is a measure of the activity of the P-glycoprotein pumps that are present in the membranes. Addition of blockers to the medium which bathes the attached membranes will block the pump and the extent of blockade is measured by a decrease of the fluorescent signal.

These systems can be used to assay the quantity of reversers available to block P-glycoprotein in the serum. The kit is preferably designed around the 96-well plastic plate format, compatible with the plate readers which are now standard in clinical laboratories. Accompanying the membranes, bound to the plates, strips, or to the paper discs, are additional miniature bottles containing a set of the reagents in appropriate amounts that will be dispensed into the wells. These reagents are the dyes Hoechst or rhodamine as the case may be, ATP, ADP, as a necessary control, magnesium chloride, and two standard amounts of a known reverser, e.g., cyclosporin, all in buffered saline. The kit is to be stored in the freezer until used by the clinical laboratory and hence will be stored in the factory and distributed commercially in low-temperature containers. This is now standard practice for many biologicals. All that the laboratory technician will have to do will be to add the strips or discs to the plates or merely set up the coated plates and then add the various additional solutions to appropriate wells of the 96-well place, add 100 microliter serum samples from the patient(s) to all the wells, add ATP, and then incubate at 37° C. for a standard time, following the change in fluorescence with time in an Elisa plate reader capable of making the fluorescent measurements, such as is available in all modem clinical laboratories. The technician will then remove the strips or paper discs and wash them, or wash off the serum from the plates with an ice-cold, saline medium containing a blocker of the multidrug resistance pump in question, and then again read the fluorescence of the strips, discs or wells, after adding a detergent to liberate the bound dye, in the case of the wells or strips. The design of the plate is such that the background instrument readings will be available as the ADP control samples in wells 1 and 2 of each 8-well row of the plate, the $3^{rd}$ and $4^{th}$ wells, and $5^{th}$ and $6^{th}$ wells will contain two concentrations of a reverser of known effectiveness that will enable the particular serum sample to be internally calibrated, while the $7^{th}$ and $8^{th}$ wells will be for the determination of the available concentration of the reverser in the patient's serum. This whole design will appear twice so as to improve the statistical reliability of the results. Appropriate software enables the flurescence readings to be directly converted into a measure of the availability of the reverser that is present in the serum of the cancer patient. Each 96 well plate system can be used to test the sera from a particular patient, or perhaps two patients, the serum samples having been taken from the patient at successive time intervals, e.g. hours to days, after the patient has received the reverser/anti-cancer drug combination.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

Thus, e.g., in an anologous manner an ex-vivo test kit for testing the effectiveness of reversers of multidrug resistance in the blood, serum or plasma of a patient containing said reversers can be prepared using cell membranes of the Multidrug Resistance-associated Protein type, the Mitoxantrone Resistance Protein type and Lung Resistance Protein Systems type.

EXAMPLE 1 a) Growth of Cells

CHO CR1R12 cells were used which are a highly drug resistant strain developed by Al-Shawi and Senior (M. K. Al-Shawi and A. E. Senior, J. Bio. Chem. 268, pg. 4197–4206 (1993) Characterization of the Adenosine Triphosphatase Activity of Chinese Hamster P-glycoprotein). They grow in α-MEM medium (Biological Industries, Kibbutz Beit Ha'emek, Israel) to which was added penicillin (100 units/mil), streptomycin (100 $\mu$g/ml), amphotericin (0.25 $\mu$g/ml), 10 $\mu$M β-mercaptoethanol, together with 10% FETAL Calf Serum (FCS) and with ribonucleosides and deoxyribonucleosides, and 5 $\mu$g/ml colchicine in 5% $CO_2$ humidified air at 37° C.

b) Preparation of Membranes

CHO CR1R12 cells were grown in complete α-MEM medium in 10–20 800 ml plastic bottles (Nunc, Denmark), in a monolayer. The cells were released from the plastic bottle before they reached confluence.

The cells were harvested in a table top centrifuge at 1000 rpm×5 min, and washed twice with 20 mM Hepes-OH pH=7.4/0.9% NaCl, and then resuspended in lysis buffer, i.e., 10 mM Hepes-Tris pH=7.4, 2 mM DTT, 5 mM EDTA, 5 mM EGTA and protease inhibitors cocktail (Sigma), and incubated in ice for 15 min.

All subsequent procedures were performed at 40. The cells were homogenized in a Teflon-glass homogenizer (40 strokes), until 70% disruption. The homogenate was centrifuged for 15 min at 3000 rpm in a table top centrifuge to spin down nuclei and unlysed cells. The supernatant was centrifuged to spin down mitochondria, in a Sorvall centrifuge in a SS34 rotor at 5500 rpm for 10 min. The supernatant was transferred to a ultracentrifuge tube and centrifuged at 35,000 rpm in a 70 Ti rotor for 45 min. The supernatant was discarded and the membrane pellet was resuspended in 500–1000 $\mu$l of lysis buffer, giving 3 to 6 mg membrane protein per ml medium. These isolated membranes were stored at −70° in aliquots.

c) Preparation of 96-well Culture Plates (hereafter "plates") Plates supplied by Nunc Corporation (Nunc/immuno™ plate (Maxisorp™ Surface) or (Nunclon™ Surface)) were used in two ways:

(i) as is (hereafter "straight")

(ii) after coating them with polylysine at concentrations of 0.2, or 1 or 5 mg/ml. Coating was performed, in all three cases, during 3 days at 37°, followed by two washes in PBS or HBS. ("PBS" is phosphate/saline buffer, pH 7.4 "HBS" is Hepes/saline buffer, pH 7.4)

In (i), the membranes to be attached (prepared as above) were added straight to the plates in an amount of 6 $\mu$g (measured by the Bradford method (reference)) in a drop of volume 1 $\mu$l HBS, and left for 30 mins at 37°, or overnight at 4°. They were then washed twice with 400 $\mu$l PBS or HBS and stored at 4° or −70°, until use. The amount of membranes that were attached as the amount of enzymatically-active P-glycoprotein were measured, compared with the activity in a standard sample of membranes in suspension. The membranes that had been attached at 37° had an enzyme activity that liberated a concentration of 41 mM phosphate in 120 mins incubation at 37°, while a suspension of membranes containing 0.3 $\mu$g liberated 15 mM phosphate in the same time. Thus some 14% of the membranes had attached. The membranes that had been attached at 4° had an enzyme activity that liberated a concentration of 52 mM phosphate in 120 mins incubation at 37°, while a suspension of membranes containing 0.6 $\mu$g liberated 32 mM phosphate in the same time. Thus some 17% of the membranes had attached.

In (ii), the membranes to be attached were added to the coated plates in an amount of 36 $\mu$g to a final volume 70 $\mu$l HBS, and left overnight at 4°. They were then washed twice with 400 $\mu$l PBS or HBS and stored at 4° or −70°, until use. As above, the amount of membranes that were attached was measured by the amount of enzymatically-active P-glycoprotein, compared with the activity in a standard sample of membranes in suspension. The membranes that had been attached to 0.2 mg/ml polylysine had an enzyme activity that liberated a concentration of 8.2 mM phosphate in 120 mins incubation at 37°, those attached to 1% polylysine liberated 10.4 mM, and those attached to 5 mg/ml polylysine liberated 12.8 mM, while a suspension of membranes containing 1.6 $\mu$g liberated 4 mM phosphate in the same time. Thus some 9, 11 and 14% of the membranes had attached.

The uptake of rhodamine to the attached membranes was measured by incubating them in the plates in 100 $\mu$l of a solution of 5 $\mu$M rhodamine, 3 mM ATP, 3 mM MgSO4, in PBS, or with 10 $\mu$M rhodamine, 6 mM ATP, 6 mM MgSO4, in 100 $\mu$l serum, at 37° for 10 mins, or without added ATP and MgSO4 for the controls. The plates were washed twice at room temperature with PBS containing 3 mM ATP, 3 mM MgSO4. To liberate the rhodamine from the membrane vesicles, 100 $\mu$l of 1% octylglucoside in PBS was added, the plate was then left for 10 mins at 37°, and the plates read at an excitation wavelength of 485 nm and emission of 530 nm. The fluorescence without added ATP was, for membranes attached by the straight method, 320 arbitrary units (fluorescence is measured on an arbitrary scale, determined for each experiment) and with added ATP, 810 arbitrary units. For membranes attached by using 5 mg/ml polylysine, the fluorescence without added ATP was, 3,000 arbitrary units, and with added ATP, 6,500 arbitrary units.

EXAMPLE 2

Blood from patients receiving blockers of P-glycoprotein is clotted or defribinated and then centrifuged to give a cell-free fluid (hereinafter called "sample"). The membranes are adsorbed to nitrocellulose paper discs and reach the clinic in this form. The discs are added to each of the 96 or 384 wells of a plastic dish. 100 microliters of the sample are added to each of the desired numbers of wells of a 96- or 384-well plastic plate. The dye Hoechst 33258 is added to the desired concentration, generally 5 microM and reading commenced in the fluorimeter at excitation of 360 nm and emission of 460 nm. At a stable baseline ATP is added to mM and readings continued. When no blocker is present, the dye is pumped out of the membranes and the fluorescence signal decreases with a half-time of some 20 minutes at 37° C. If a blocker of P-glycoprotein is present and effective, the rate of pumping out of the dye is lowered. The ratio of the half-time of efflux of dye in the patient's sample to the rate for a standard sample prepared from blood that was not exposed to the blocker gives a measure of the effectiveness of the blocker present in the patient's sample. If the blocker is ineffective in the patient, the half-time of efflux of dye will be the same as with the sample that never received a blocker. If the blocker is effective, the half-time will be substantially increased, ten to twenty-fold. It has been found that the effectiveness of known blockers of P-glycoprotein, added to serum from healthy patients, can be quantitated accurately by observing the increase in half-time of the pumping out of the dye.

As noted in Example 2, there is described the measurement of the effect of the blocker present in the patient's serum as it is active against the H-site of P-glycoprotein. Example 1 describes, in contrast, the measurement of the effect of blocker against the R-site of P-glycoprotein. Both pieces of information are relevant to the clinician since some chemotherapeutic drugs are transported by the H-site and others by the R-site of P-glycoprotein.

As will be realized, a main advantage and feature of the present invention is to provide a procedure which will enable the clinician to measure ex vivo the bioavailability of drugs in the serum of patients receiving pump blockers. By suspending in, or attaching the membranes to, the plastic wells or to paper discs, the reaction with the membrane-based pumps is allowed to take place ex vivo but in the serum of the patient, in conditions that mimic those in his/her blood. The fact that the membranes are so affixed enables the serum to be easily and rapidly washed off after the reaction with the dye (merely by flipping over the plate, or transferring the discs), thus enabling a highly sensitive assay of the effectiveness of the reverser in spite of the serum which can interfere with a direct reading of the fluorescence signals. In addition, use of the two assay systems together enables the effectiveness of the blockers of P-glycoprotein to be measured against both its drug-binding sites, doubling the amount of information available to the clinician.

Thus the invention provides a new method for the easy, rapid measuring of the effectiveness of the reversers of multidrug resistance which are now entering into clinical trials and soon, into the hospital.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. An ex-vivo test kit for testing the effectiveness of reversers of multidrug resistance in the blood, serum or plasma of a patient containing said reversers, said kit comprising:
    a) a plurality of cell membranes from drug-resistant cells, said cell membranes containing proteins which pump drugs and said membranes being respectively attached to a plurality of support surfaces; and
    b) a dye which provides a light signal, which dye is pumped by said proteins contained in said membranes out of said membranes and into membrane sacs that are attached to said support surfaces.

2. An ex-vivo test kit according to claim 1, wherein said kit further comprises reagents for activating said pump.

3. An ex-vivo test kit according to claim 2, wherein said reagents comprise a combination of adenosine triphosphate and magnesium.

4. An ex-vivo test kit according to claim 1, wherein said dye is pumped into closed vesicles by said proteins contained in said membranes.

5. An ex-vivo test kit according to claim 1, wherein said dye is pumped out of said membranes by said proteins contained in said membranes.

6. An ex-vivo test kit according to claim 1, wherein said kit further comprises blockers of said pump as positive control means.

7. An ex-vivo test kit according to claim 1, wherein said surfaces are the surfaces of a plurality of wells.

8. An ex-vivo test kit according to claim 1, wherein said surfaces are a plurality of plastic, comb-like teeth.

9. An ex-vivo test kit according to claim 1, wherein said support surfaces are a plurality of filter paper elements.

10. An ex-vivo test kit according to claim 9, wherein said filter paper elements are sized to be individually inserted in the wells of a multi-well plate.

11. An ex-vivo test kit according to claim 1, wherein said dye is a fluorescent dye which provides a fluorescence signal.

12. A method for testing the effectiveness of reversers of multidrug resistance in the blood, serum or plasma of a patient containing said reversers, said method comprising providing a plurality of cell membranes from drug-resistant cells, said cell membranes containing proteins which pump drugs and said membranes being attached to a plurality of support surfaces and a fluorescent dye which provides a fluorescence signal, which dye is pumped by said proteins contained in said membranes, out of said membranes and into membrane sacs that are attached to said support surfaces and bringing said membrane-containing support surfaces into contact with the blood, serum or plasma of a patient containing said reversers, adding reagents for activating said pump and noting the results thereof by measuring the change of the fluorescent signal emitted by the dye.

13. A method according to claim 12, wherein said surfaces are the surfaces of a plurality of wells.

14. A method according to claim 12, wherein said surfaces are a plurality of plastic, comb-like teeth.

15. A method according to claim 12, wherein said support surfaces are a plurality of filter paper elements.

16. The ex-vivo test kit according to claim 1 wherein the proteins are P-glycoproteins, multidrug resistance-associated proteins, mitoxantrone resistance proteins or lung resistance proteins.

17. The method according to claim 12 wherein the proteins are P-glycoproteins, multidrug resistance-associated proteins, mitoxantrone resistance proteins or lung resistance proteins.

18. The ex-vivo test kit according to claim 1 wherein the proteins are P-glycoproteins.

19. The method according to claim 12 wherein the proteins are P-glycoproteins.

* * * * *